US008819991B2

(12) United States Patent
Schafer et al.

(10) Patent No.: US 8,819,991 B2
(45) Date of Patent: Sep. 2, 2014

(54) METHOD FOR SEED DEVITALIZATION

(71) Applicant: Dow AgroSciences LLC, Indianapolis, IN (US)

(72) Inventors: Barry W. Schafer, Cicero, IN (US); Rod A. Herman, New Ross, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 0 days.

(21) Appl. No.: 13/771,879

(22) Filed: Feb. 20, 2013

(65) Prior Publication Data

US 2013/0160168 A1 Jun. 20, 2013

Related U.S. Application Data

(63) Continuation of application No. 13/412,474, filed on Mar. 5, 2012, now abandoned, which is a continuation of application No. 12/509,806, filed on Jul. 27, 2009, now Pat. No. 8,153,864.

(60) Provisional application No. 61/087,843, filed on Aug. 11, 2008.

(51) Int. Cl.
*A01H 5/10* (2006.01)
*A01H 5/00* (2006.01)
*A01H 3/00* (2006.01)

(52) U.S. Cl.
CPC ... *A01H 5/10* (2013.01); *A01H 3/00* (2013.01)
USPC ...... 47/58.1 SE; 800/298; 800/306; 800/312; 800/314; 800/320.1

(58) Field of Classification Search
CPC ......... C07K 14/415; A01H 5/00; A01H 1/00; A01H 5/10; A01N 59/00
USPC ...................... 800/298, 306, 312, 314, 320.1; 47/58.1 SE
See application file for complete search history.

(56) References Cited

U.S. PATENT DOCUMENTS

| | | | |
|---|---|---|---|
| 3,635,728 A | 1/1972 | Rockland | |
| 4,436,757 A | 3/1984 | Lange et al. | |
| 5,211,983 A | 5/1993 | Bley | |
| 8,153,864 B2 | 4/2012 | Schafer et al. | |
| 2004/0053204 A1* | 3/2004 | Morris et al. | 435/1.1 |
| 2006/0179511 A1* | 8/2006 | Chomet et al. | 800/278 |
| 2007/0202202 A1* | 8/2007 | Kwon et al. | 424/757 |
| 2008/0256667 A1 | 10/2008 | Dersch et al. | |
| 2009/0133165 A1* | 5/2009 | Guy et al. | 800/298 |

OTHER PUBLICATIONS

Bai et al. Winterfat (Eurotia lanata (Pursh) Moq.) Seedbed Ecology: Low temperature exotherms and cold hardiness in hydrated seeds as influenced by imbition temperature. Annuals of Botany 81: 595-602, 1998.*
Boucaud et al. The use of 1,2-propanediol for cryopreservation of recalcitrant seeds: The model case of Zea Mays imbibed seeds. Cryo-Letters 9. 94-101, 1988.*
Lambardi et al. Cryopreservation as a tool for the long-term conservation of woody plant germplasm: develop-ment of the technology at the CNR/IVALSA Institute of Florence. The Role of Biotechnology, villa Gualino, Turin, Italy—Mar. 5-7, 2005, pp. 181-182.*
Anchordoquy et al., Frontiers in Clinical Research, Preservation of DNA, Cell Preservation Technology, 2007; 5 (4):180-188.
Buitink et al., Molecular Mobility in the Cytoplasm: An Approach to Describe and Predict Lifespan of Dry Germplasm, PNAS, Feb. 29, 2000, 97(5):2385-2390.
International Search Report for International Application No. PCT/US09/52221 mailed Sep. 22, 2009, 3 pages.
International Written Opinion for International Application No. PCT/US09/52221 mailed Sep. 22, 2009, 5 pages.
Saha et al., Cotton Improvement, Effect of lyophilization of Cotton Tissue on Quality of Extractable DNA, RNA, and Protein, The Journal of Cotton Science, 1997;1:10-14.
Schafer et al., Devitalization of Transgenic Seed That Preserves DNA and Protein Integrity, Journal of Biomolecular Techniques, 2008; 19:348-352.
Vertucci et al., Theoretical Basis of protocols for Seed Storage III. Optimum Moisture Contents for Pea Seeds Stored at Different Temperatures, Annals of Botany, 1994; 74:531-540.
Vertucci et al., Theoretical Basis of Protocols for Seed Storage, Plant Physiol., 1990; 94:1019-1023.
Vertucci, Effects of Cooling Rate on Seeds Exposed to Liquid Nitrogen Temperatures, Plant Physiol., 1989; 90:1478-1485.
Walters, Temperature Dependency of Molecular Mobility in Preserved Seeds, Biophysical Journal, Feb. 2004; 86:1253-1258.
NDSU Extension Service. Freezing Corn, retrieved on Jul. 5, 2011. Retrieved from the Internet at http://wwww.est.nodak.edu/extnews/askext/ freezing/4424.htm, 2 pp.
Sudarmonowati et al. Cryopreservation of true-see and embryo of maize and soybean for long-term storage. Indonesian Journal of Agricultural Science 2(2) 2001: 31-36.

(Continued)

*Primary Examiner* — June Hwu
(74) *Attorney, Agent, or Firm* — Eric J. Kraus; TraskBritt P.C.

(57) ABSTRACT

The invention provides a method for devitalizing plant seed, the method comprising the steps of hydrating a viable whole plant seed and freezing the hydrated whole plant seed. The invention further provides a collection of devitalized whole plant seed wherein the integrity of genomic DNA and protein within the devitalized plant seed is preserved.

16 Claims, No Drawings

(56) References Cited

OTHER PUBLICATIONS

International Preliminary Report on Patentability for International Application No. PCT/US09/52221 Feb. 15, 2011, 6 pp.

Jimenez-Lopez et al., Expression Profile of Maize (*Zea mays* L.) Embryonic Axes During Germination: Translational Regulation of Ribosomal Protein mRNAs, Plant & Cell Physiology, Jul. 26, 2011, pp. 1719-1733, vol. 52 issue 10, Oxford University Press.

\* cited by examiner

METHOD FOR SEED DEVITALIZATION

CROSS-REFERENCE TO RELATED APPLICATIONS

This application is a continuation of U.S. patent application Ser. No. 13/412,474, filed Mar. 5, 2012, abandoned, which is a continuation of U.S. patent application Ser. No. 12/509,806, filed Jul. 27, 2009, now U.S. Pat. No. 8,153,864, issued Apr. 10, 2012, which claims the benefit of U.S. Provisional Patent Application No. 61/087,843, filed on Aug. 11, 2008, each of which is expressly incorporated by reference herein.

TECHNICAL FIELD

The present invention relates to a method for devitalizing seed.

BACKGROUND OF THE INVENTION

Agricultural biotechnology companies are required to provide intact transgenic seed to various agencies as part of the global regulatory approval process. Provision of devitalized seed is preferred as a result of intellectual property and product stewardship considerations.

Plant seeds include a germination step or phase as part of their growth cycle. In general, germination refers to the resumption of growth by an embryo in a seed after a period of dormancy. This resumption of growth occurs when a seed is exposed to suitable environmental conditions, including suitable temperature, adequate water and oxygen. Seeds, even in dormancy, are respiring, but at a very slow rate. As the heat increases, the respiration rate will increase, regardless of the other conditions present. Absent proper temperature, moisture and oxygen, a seed will remain dormant.

Many food stuffs for human consumption are seeds. These include cereal, grains, rice, wheat, corn, barley and oats. Plant seeds are also used in or as medicinal products (e.g., linseed oil and soybean oil) and clothing (e.g., cotton seed). In some cases, seeds cannot be used as intended if germination occurs. In the case of popcorn seed, the need to terminate germination is especially important. Several countries, including Australia, do not allow importation of popcorn seed absent proof of complete seed devitalization.

Currently, dehydration is used to suppress undesired germination in seed products. Dehydration techniques can preclude germination; however, in some cases these techniques have an unacceptable effect on final product quality. Other commonly used methodologies for seed devitalization, such as heating or autoclaving, have the unwanted consequence of degrading the protein and/or the DNA, thereby rendering the seed unfit as a reference material for use in protein or DNA detection assays. Though individual seeds may be devitalized by quartering, this procedure is labor intensive.

Accordingly, a need exists to provide a simplified methodology for devitalizing seed while maintaining protein and DNA integrity. The present invention addresses and solves the problems attendant upon conventional processes for devitalizing seed.

SUMMARY OF THE INVENTION

The invention provides a method for devitalizing plant seed, the method comprising the steps of hydrating a viable whole plant seed and freezing the hydrated whole plant seed.

The invention further provides a collection of devitalized whole plant seed wherein the integrity of genomic DNA and protein within the devitalized plant seed is preserved.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the description is to be regarded as illustrative in nature, and not as restrictive.

DETAILED DESCRIPTION OF THE INVENTION

The present invention provides a method for devitalizing plant seed, the method comprising the steps of hydrating a viable whole plant seed and freezing the hydrated whole plant seed.

As used herein the term "devitalize" refers to destroying the ability of a seed to germinate under otherwise acceptable germination conditions (i.e., adequate water, oxygen and temperature).

The plant seed to which the present invention is applicable includes any viable whole plant seed. The invention is particularly useful for inbred and hybrid corn seeds, but is also useful for other seeds, for example soybean, canola and cotton seeds, as well as other crop seeds.

As used herein, the term "whole" means a seed that has not been purposefully separated into its constituent parts (e.g., for corn, the hull, endosperm, tipcap, pericarp, and germ). The whole corn may or may not have been cracked, cut or abraded. Purposeful separation of one constituent from another does not include random separation that may occur during storage, handling, transport, or cutting.

An initial step in the present invention is to hydrate viable whole plant seed. As used herein, the term "hydrate" means to cause to take up an aqueous solution such as through contacting the seed to an aqueous solution (e.g., immersing the seed in deionized water or buffer).

A further step in the present invention is to freeze the hydrated whole plant seed. As used herein, the term "freeze" means to pass from the liquid to the solid state by loss of heat or to convert into a frozen state. The freezing step can be accomplished with either cold air, liquid nitrogen, or liquid carbon dioxide. Rapid or quick freezing may also be employed, which generally involves reducing the temperature of the seed to below 0° C. (such as between 0° C. to −20° C., more preferably −20° C. to −196° C.) in a period of time of two hours or less.

An optional step in the present invention is to freeze-dry the frozen whole plant seed. Freeze-drying is a well-established process for drying, and thereby preserving, pharmaceuticals such as antibiotics, vitamin preparations, vaccines, etc. Aqueous products to be dried are first frozen solidly and are then subjected to a high vacuum and a controlled heat input. Under these conditions, the water content of the product goes directly from ice to water vapor, by-passing the intermediary liquid phase. This large quantity of sublimating water vapor cannot be pumped out of the system directly by oil sealed rotary vacuum pumps, since the oil therein will quickly become contaminated by water condensing in the oil, resulting in too high a pressure for satisfactory operation. To prevent this from occurring, a refrigerated condenser, connected between the drying chamber and the vacuum pump, freezes out the water vapor on coils, cold surfaces, etc. Alternatively, a chemical desiccant can be used to sequester the sublimating water vapor.

Example 1

A collection of HERCULEX® I hybrid maize seed, non-transgenic maize seed, WIDESTRIKE® cotton seed and non-transgenic cotton seed were separately soaked in deionized water overnight at 4° C. in the dark. Holding the seeds at a cold temperature (~4° C.) during the hydration process may help inhibit proteases that could effect protein composition. The following day, the water was decanted and the hydrated seeds were fully submersed in liquid nitrogen and frozen for 3-5 minutes. The liquid nitrogen was decanted and the seeds were collected in a vessel and lyophilized.

Example 2

The treated seeds from Example 1 were analyzed for viability. Germination tests with 100 seeds per treatment (non-treated maize, devitalized maize, non-treated cotton, and devitalized cotton) were placed on moist indented germination pads (Seedsburo Equipment Co., Chicago, Ill.) in plastic Petri dishes at 27° C. in the dark for up to 7 days. Numbers of germinated and non-germinated seed were counted and recorded. A germination test demonstrated that 100% of the treated seed was nonviable after this simple procedure.

Example 3

After the treated seeds were shown to be devitalized, several seeds were finely ground in an IKA-Werke MF-10 grinder (Staufen, Germany) for subsequent protein and DNA characterization. The remaining seeds were kept at room temperature to assess long-germ stability. It was found that the method of the present invention kept the seed intact, and allowed for the seed to be stored at room temperature for at least 6 months with no noticeable degradation.

Example 4

Samples of the ground cotton seed tissue (approximately 15 mg) were analyzed for Cry1F, Cry1Ac and PAT proteins, and samples of the ground maize seed tissue were analyzed for Cry1F, using commercially available ELISA kits and validated Dow AgroSciences methods. The PAT protein is non-detectable in HERCULEX® I maize seed, so this ELISA was not conducted on the maize seed. The proteins were extracted from seed samples in microfuge tubes with a PBST (Sigma Chemical, St Louis, Mo.) solution and two inch steel ball bearings in a bead mill (Geno-Grinder, BT&C/OPS Diagnostics, Bridgewater, N.J.) for 3 minutes at 1500 strokes/min. The extract was centrifuged; the aqueous supernatant was collected, diluted and assayed using specific Cry1F, Cry1Ac and PAT ELISA kits developed by Strategic Diagnostics Inc. (Newark, Del.) for Cry1F and Cry1Ac, and Envirologix Inc. (Portland, Me.) for PAT. Serial dilutions of each sample (treated and non-treated seeds of the transgenic and conventional control) were incubated in the wells of an anti-Cry1F, anti-Cry1Ac or anti-PAT antibody coated plate. After a washing step, an aliquot of enzyme-conjugated anti-Cry1F, Cry1Ac or anti-PAT antibody was added and incubated in the plate to form an antibody-protein-antibody/enzyme conjugate sandwich. At the end of this incubation period, the unbound reagents were removed from the plate by washing with PBST. The presence of the three proteins was detected by incubating the antibody-bound enzyme conjugates with an enzyme substrate, generating a colored product. Since the proteins are bound in the antibody sandwich, the level of color development is related to the concentration of the Cry1F, Cry1Ac, or PAT in the sample (i.e., lower protein concentrations result in lower color development). The absorbance at 450 nm minus 650 nm was measured using a spectrophotometric plate reader and compared to a standard curve to obtain quantitation of the transgenic proteins in the seed tissue extracts. Quantitative ELISA analysis of the Cry1F protein in both maize and cotton was shown to be unaffected. In addition, the Cry1Ac and PAT proteins within the devitalized and viable cotton seed were present at equivalent amounts.

Example 5

Samples for SDS-PAGE were prepared from finely-ground seeds from each treatment of the transgenic and conventional controls. Approximately 50 mg of maize seed and 150 mg of cotton seed was extracted in 1 mL of PBST (Sigma, St. Louis, Mo.) for 3 minutes in a bead mill at 1500 strokes/min. Three inch ball bearings were added to the microfuge tubes to facilitate the grinding process. After grinding, the soluble protein was collected by centrifuging the sample for 5 min. at ~10,500×g. As a positive control consisting of 1-2 ng of microbe-derived Cry1F protein was dissolved in 10 μL of PBST. The samples were mixed with Laemmli buffer containing 2.5% 2-mercaptoethanol, heated for 5 min at ~100° C., and separated on polyacrylamide gels from Bio-Rad (Hercules, Calif.). Two gels were prepared and one SDS-PAGE gel was stained with GelCode Blue (Pierce Chemical, Rockford, Ill.) total protein stain and the other gel was transferred onto a nitrocellulose membrane (Bio-Rad) for western blot analysis. The analysis was carried out essentially as described in the Protein Electrophoresis Applications Guide from Hoefer Scientific (San Francisco, Calif.). The blot was probed with an anti-Cry1F polyclonal antibody from Strategic Diagnostics and detected with a horseradish peroxidase-labeled goat anti-rabbit polyclonal antibody from Bio-Rad. Immunospecific bands were visualized by exposing the membrane to CL-XPosure X-ray Film from Pierce. The total extractable protein of the devitalized seeds was unchanged as demonstrated by SDS-PAGE analysis. The protein profiles were identical and the Cry1F protein was equivalent in both the devitalized and control seed of both crops. The full-length Cry1F, which is very susceptible to proteases, was maintained in the cotton seed.

Example 6

Southern blot analysis was performed on DNA isolated from maize and cotton seeds to investigate the stability of the genomic DNA. Genomic DNA was isolated from maize seeds using a modified CTAB extraction protocol as described by Richards, Reichardt and Rogers and further purified by using Genomic-tips according to the QIAGEN (Valencia, Calif.) Genomic DNA Handbook. The DNA was quantified using picogreen (Invitrogen, Carlsbad, Calif.), and 10 μg of genomic DNA from each of the treated and the non-treated seed lots was independently digested with Hind III restriction enzyme. Positive control samples for hybridization were prepared by combining plasmid or fragment DNA with genomic DNA from the conventional control and digested using the same procedures and restriction enzyme as the test samples. DNA from the conventional control seeds was digested using the same procedures and restriction enzyme as the test samples. DNA from the conventional control seeds was digested using the same procedures and restriction enzymes as the negative controls. The digested DNA was resolved on a 0.8% agarose gel and transferred on to positively charged nylon membranes according to Sambrook and Russell. DNA probes specific for the Cry1F gene and a 1-kb ladder molecular size marker (Invitrogen) were radioactively labeled with [($\alpha$-$^{32}$P]dCTP. This was accomplished using PRIME-IT® Random Primer Labeling Kit (Stratagene, La Jolla, Calif.) and ProbeQuant G-50 Micro Columns (GE Healthcare, Piscataway, N.J.) according to manufacturer's suggested procedures. Prehybridization and hybridization reactions were carried out according to Sambrook and Russell. After hybridization, the membranes were washed and exposed to X-ray film (Pierce) sandwiched between two intensifying screens for two days.

Using a radioactively labeled probe for the Cry1F gene, comparisons of the southern blot hybridization patterns of the treated and untreated seeds were possible using genomic DNA digested with the endonuclease HindIII. Hybridization patterns for Cry1F gene were identical for both treated and untreated seeds of both maize and cotton. These data indicate that the devitalization procedure described here maintained the genomic DNA and did not affect the quality of the DNA. All of the positive plasmid and fragment controls hybridized with the Cry1F gene probes at the expected molecular weight. The Cry1F did not hybridize to the conventional control DNA.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method for devitalizing a viable whole plant seed containing at least one transgenic protein and at least one non-transgenic protein, the method comprising the steps of:
   a) hydrating the viable whole plant seed; and,
   b) freezing the hydrated whole plant seed to produce a devitalized whole plant seed, wherein integrity of genomic DNA and protein within the devitalized plant seed is preserved, wherein the at least one transgenic protein in the viable whole plant seed and the at least one transgenic protein in the devitalized whole plant seed are present at equivalent amounts, and wherein the total extractable protein in the viable whole plant seed and the total extractable protein in the devitalized whole plant seed are present in equivalent amounts.

2. The method of claim 1, further comprising the step of freeze drying the frozen whole plant seed.

3. The method of claim 1, wherein the viable whole plant seed is hydrated by contacting the seed with an aqueous solution.

4. The method of claim 3, wherein the aqueous solution is deionized water.

5. The method of claim 1, wherein the hydrated whole plant seed is frozen by contacting the seed with a liquid cryogen.

6. The method of claim 2, wherein the frozen whole plant seed is freeze dried by lyophilization.

7. The method of claim 1 wherein the viable whole plant seed is viable whole corn or cotton seed.

8. The method of claim 1, wherein a bulk sample of viable whole plant seed is devitalized.

9. The method of claim 1, wherein the viable whole plant seed is not autoclaved or subjected to an inert gas and heat of at least 40° C.

10. The method of claim 1, wherein freezing the hydrated whole plant seed comprises freezing the frozen whole plant seed at a temperature between 0° C. and −20° C.

11. The method of claim 1, wherein freezing the hydrated whole plant seed comprises freezing the frozen whole plant seed in a period of time of two hours or less.

12. The method of claim 1, wherein freezing the hydrated whole plant seed comprises freezing the frozen whole plant seed with cold air.

13. The method of claim 1, wherein freezing the hydrated whole plant seed comprises freezing the frozen whole plant seed with liquid nitrogen.

14. The method of claim 1, wherein freezing the hydrated whole plant seed comprises freezing the frozen whole plant seed with liquid carbon dioxide.

15. The method of claim 1 wherein the viable whole plant seed is a viable whole plant seed selected from the group consisting of viable whole soybean, canola, and cotton seed.

16. The method of claim 1, further comprising:
   isolating genomic DNA or protein from the devitalized plant seed; and
   determining that the integrity of the genomic DNA or protein within the devitalized plant seed is preserved.

* * * * *